United States Patent [19]

Sawai et al.

[11] Patent Number: 4,914,121
[45] Date of Patent: Apr. 3, 1990

[54] 3-PHENYL-1-PHENYLPYRAZOLE-4 ACETIC ACID COMPOUNDS WHICH ARE USEFUL IN TREATING IMMUNE DISEASES

[75] Inventors: Kiichi Sawai; Masayasu Kurono; Takahiko Mitani; Kazumi Niu; Kyoichi Asano, all of Aichi, Japan

[73] Assignee: Sanwa Kagaku Kenkyusho Co., Ltd., Nagoya, Japan

[21] Appl. No.: 266,280

[22] Filed: Oct. 26, 1988

Related U.S. Application Data

[62] Division of Ser. No. 137,217, Dec. 22, 1987, abandoned.

[30] Foreign Application Priority Data

Dec. 26, 1986 [JP] Japan .................................. 61-308588
Mar. 5, 1987 [JP] Japan .................................. 62-51030

[51] Int. Cl.⁴ ..................... A61K 31/45; C07D 231/12
[52] U.S. Cl. ..................................... 514/406; 548/378
[58] Field of Search ......................... 548/378; 514/406

[56] References Cited

U.S. PATENT DOCUMENTS 4,042,706 8/1977 Ahrens et al. ........................ 548/378
4,146,721 3/1979 Rainer ................................. 548/378

OTHER PUBLICATIONS

Chemical Abstracts, vol. 79, No. 1, Abstract 42498e, Aug. 20, 1973.
Chemical Abstracts, vol. 82, No. 10, Abstract 72987t, Mar. 10, 1975.

*Primary Examiner*—Mary C. Lee
*Assistant Examiner*—Zinna Northington
*Attorney, Agent, or Firm*—Armstrong, Nikaido, Marmelstein, Kubovcik & Murray

[57] ABSTRACT

A pharmaceutical composition comprising as an effective ingredient, a pyrazole compound of the formula

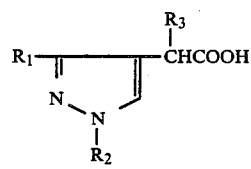

wherein each of $R_1$ and $R_2$ is phenyl or p-halogenophenyl radical, respectively, and $R_3$ is hydrogen atom or methyl radical, or a salt thereof. The composition is used for curing immunity diseases and a nephropathy.

6 Claims, 8 Drawing Sheets

Significance difference:
  ★   : p < 0.05
  ★★  : p < 0.01
  ★★★ : p < 0.001

BL   : C57BL mice (6 heads)
Cont : Control (administrating no drug)
Indo : Indomethacin
CCA  : Robenzarit
Cy   : Cycrophostamide

FIG. 7

3-PHENYL-1-PHENYLPYRAZOLE-4 ACETIC ACID COMPOUNDS WHICH ARE USEFUL IN TREATING IMMUNE DISEASES

This application is a division of application Ser. No. 137,217 filed Dec. 22, 1987, now abandoned.

BACKGROUND OF THE INVENTION

1. Field of the Invention

The present invention relates to a pharmaceutical composition and more particularly to that for medical treating immunity diseases and a nephropathy.

2. Related Arts

It has been known that pyrazole compounds represented by the following formula, and more particularly 3-(p-chlorophenyl)-1-phenylpyrazole-4-acetic acid (generally called as Lonazolac) has pharmaceutical activities of antiinflammatory, antipyretic action and sedative action and shows a relatively low toxicity (BP 1373212 and U.S. Pat. No. 4146721).

wherein each of $R_1$ and $R_2$ is phenyl or p-halogenophenyl radical, respectively, and $R_3$ is hydrogen atom or methyl radical.

Further, it has been reported that the pyrazole compounds of said formula and other than said specified compound also show antiinflammatory ["Rinsyo Meneki" (may be translated as Cinical Immunity) Vol. 18, page 387 (1986)].

While, as an ingredient for curing a nephropathy, a diuretic drug has generally been employed. It is required for attaining the purpose, however, to give the drug over a relatively long period of time. As a result, the drug may show a toxicity due to its accumulation or an intercurrent disease is apt to be ocurred. Therefore, it has eargerly been required for a more safety drug for curing the nephropathy.

SUMMARY OF THE INVENTION

An action of antiinflammatic agent to immunity system has been noted with great interest, in connection with prostaglandin. In view of this view point, the pyrazole compounds shown by said formula are effective for curing immuno-acceleratory diseases but give a bad effect to immuno-inhibitory diseases and thus so considered that this type medicine should not be dosed to the patient with the latter immunity disease.

The present inventors have, however, found through their careful study and investigation that the immuno-inhibitory action of the compounds shown by the formula, which has been commonly considered from the antiinflammatory action thereof is not correct but, in actual, the compounds show an immunity controlling or regulating action.

Therefore, one of the objects of the invention lies in use the compound(s) shown by the formula, as an immunity controlling ingredient to cure various immunity diseases.

According to the invention, the object can be attained by an immunity control composition comprising an effective amount of a pyrazole compound of the formula wherein each of $R_1$ and $R_2$ is phenyl or p-halogenophenyl radical, respectively, and $R_3$ is hydrogen atom or methyl radical, or a pharmaceutically acceptable salt thereof, together with a pharmaceutically acceptable carrier.

In view of the immunity controlling action of the compounds, the inventors have further studied and investigated to utilize the compounds as an drug for medical treating the nephropathy and finally found that it is effective therefor, especially to glomerulitis, chronic nephritis and nephrose.

Therefore, another object of the invention is to provide a composition for medical treating with nephropathy, which does not show or shows a relatively low toxicity and causes almost no intercurrent disease due to its side effect, even if it will be administrated over a long period of time.

According to the invention, this object can be attained by a pharmaceutical composition for medical treating nephropathy, which comprises an effective amount of the pyrazole compound shown by said formula, or a pharmaceutically acceptable salt thereof, together with a pharmaceutically acceptable carrier.

Among the compounds represented by said Formula, exemplar one to be employed as the effective ingredient for the pharmaceutical composition according to the invention may be shown in following Table 1.

TABLE 1

| Comp. | $R_1$ | $R_2$ | $R_3$ | Salt | m.p. |
|---|---|---|---|---|---|
| 1 | Cl-⟨⟩- | ⟨⟩- | H | — | 150 (°C.) |
| 2 | Cl-⟨⟩- | ⟨⟩- | H | Ca | 270 |
| 3 | F-⟨⟩- | ⟨⟩- | H | — | 150 |
| 4 | Cl-⟨⟩- | ⟨⟩- | —CH₃ | — | 180 |
| 5 | ⟨⟩- | F-⟨⟩- | H | — | 126 |
| 6 | ⟨⟩- | ⟨⟩- | H | — | 275 |
| 7 | Br-⟨⟩- | ⟨⟩- | H | — | 141 |

Each of the compounds shown by said Formula shows, in general, a low solubility to water, ether or the like usual solvent and thus, when the compound is made into a medicine, the pharmaceutically acceptable carrier can be employed for improving its solubility and to stabilize the same. As the carrier, natural high molecular substances, for instance, gelatin, chitin, chitocine, aliphatic acid esters thereof and the like; synthetic high molecular substances, for instance, cellulosic, vinylic, acrylic, glycolic and the like synthetic polymers; succharoids, for instance, lactose, starch, cellurose, cyclic dextrin or the like; and any mixture of these substances may be listed.

For preparing the medicine, a filler, binder, disintegrator or the like additive may be composed, in addition to the carrier, but such additive should, of course, be selected from those having no physicochemical reaction with the compound shown by said Formula, as the main ingredient and established as inactive in a retarded immuno-reactive test from the pharmacological view point.

The compound and/or salt thereof can be made into the medicine without any special limitation. A formulation for the medicine is carried out in a conventional manner to form a tablet, capsule, granule, powder or the like solid one, injection, solution or oral administration, embrocation or the like liquid one, ointment, jelly or the like semi-solid one. A dosing amount of the compound or salt for human depends on a kind of same, a symptom of the patient, form of the medicine and other factors but, in general, is selected in a range of 10 to 1500 mg/day for an adult. In case or oral dosage, however, about 150 mg/day is preferable for the adult.

PREFERRED EMBODIMENTS OF THE INVENTION

The invention will now be further explained with reference to Examples for preparing a medicine and Pharmacological Test Examples.

Please note that the compound employed for the Examples was Compound 2 in said Table 1, namely calcium salt of 3-(p-chlorophenyl)-1-phenylpyrazole-4-acetic acid (hereinafter referred to as compound 2).

EXAMPLE 1

(Injection)

To 0.1% aqueous solution of saccharoaliphatic acid ester, the compound 2 and mannitol were added to make a concentration thereof in 1.5% and 2%, respectively and then the mixture was stirred to dissolve the substances. The resulting solution was filtered for debacterization, charged into vials by each 2 ml and freeze dried to seal the same.

This dry powder accommodated in the vial can be dissolved in a physical saline, when it should be injected to a patient.

EXAMPLE 2

(Embrocation)

To 0.2% aqueous solution of saccharoaliphatic acid ester, the compound 2 was added to make its concentration in 0.2% and the mixture was stirred to dissolve the compound and to obtain a desired embrocation.

This embrocation can directly be applied on skin or mucosa.

EXAMPLE 3

(Ointment)

To 0.5% aqueous solution of saccharoaliphatic acid ester, the compound 2 was added to make its concentration in 0.2% and the mixture was stirred to dissolve the compound. The resulting solution was spray-dried to obtain a powdery composition. The composition and other ingredients were composed under the following prescription to prepare a desired ointment, in a conventional manner.

| Ingredient | Amounts (g) |
| --- | --- |
| Said composition | 0.5 |
| Diethyl sebacinate | 8.0 |
| Spermaceti | 5.0 |
| Sodium phosphate of polyoxyethyleneoilether | 6.0 |
| Sodium benzoate | 0.5 |
| Vaseline | remainder |
| | Total 100.0 (g) |

EXAMPLE 4

(Suppository)

The powdery composition obtained by the way of the procedure in Example 3 was dispersed in a molten higher fatty acid glyceride under the following prescription to prepare a desired suppository, in a conventional manner.

| Ingredient | Amount (mg) |
| --- | --- |
| Said composition | 60 |
| Fatty base (Cacao fat) | 1640 |
| | 1700 mg/piece |

EXAMPLE 5

(Tablet)

The compound 2 and hydroxypropylcellulose were mixed in weight ratio of 1:3 and the mixture was milled to obtain a powdery composition. The composition and other ingredient were composed under the following prescription and treated in a conventional manner to prepare desired tablets.

| Ingredient | Amount (mg) |
| --- | --- |
| Said composition | 100 |
| Lactose | 85 |
| Carboxymethylcellulose (Ca salt) | 7 |
| Silicic anhydride | 1 |
| Magnesium stearate | 7 |
| | 200 mg/tablet |

EXAMPLE 6

(Capsule)

The powdery composition obtained by the way of the procedure in Example 5 and other ingredients were composed under the following prescription and treated and filled in a gelatin capsule, in a conventional manner to prepare a desired preparation.

| Ingredient | Amount (mg) |
| --- | --- |
| Said composition | 100 |
| Lactose | 97 |
| Hydroxypropylcellulose | 2 |
| Magnesium stearate | 1 |
| | 200 mg/capsule |

PHARMACOLOGICAL TEST EXAMPLE 1

(Actual use of ointment)

The ointment obtained by the procedure of Example 3 was given to each of volunteers (20 persons) who have a rubefaction due to a bite or hemorrhoid, or a monopathy due to ascariasis or the like, to use the ointment freely.

Thereafter, an opinionaire research was made to obtain results as shown in following Table 2. As seen from the Table, all most all of the persons have reported that the ointment imroves the condition.

TABLE 2

| | Persons | | |
| --- | --- | --- | --- |
| Item | Improved | Doubtful | Ingravescense |
| Rubefaction | 18 | 1 | 1 |
| Ascariasis | 16 | 3 | 1 |

PHARMACOLOGICAL TEST EXAMPLE 2

(Influence on productivity of antibody)

(a) Object

An influence of the compound 2 on productivity of an antibody is checked by sensitizing normal mice with an antigen in an amount for developing an immuno-response to its maximum level due to sufficient stimulation by the antigen, or in another amount which causes no sufficient proceeding of immuno-response due to insufficient stimulation by the antigen, and then administrating the compound.

(b) Operation

Each group of BALB/c mice was sensitized by injecting from tail vein a sheep erythrocyte (SRBC, $2 \times 10^8$ or $2 \times 10^7$ pieces), as the antigen. While, the compound suspended in 5% gum arabic solution was orally dosed to the mice in an amount of 0.1, 1, 10 or 100 mg/kg in twice of just after the sensitization and the next day thereof.

On the 4th day after the sensitization, the spleen was enucleated and number of PFC in spleen cells was determined to make the number as an index for ability on antibody production.

(c) Result and consideration

Figure 1:
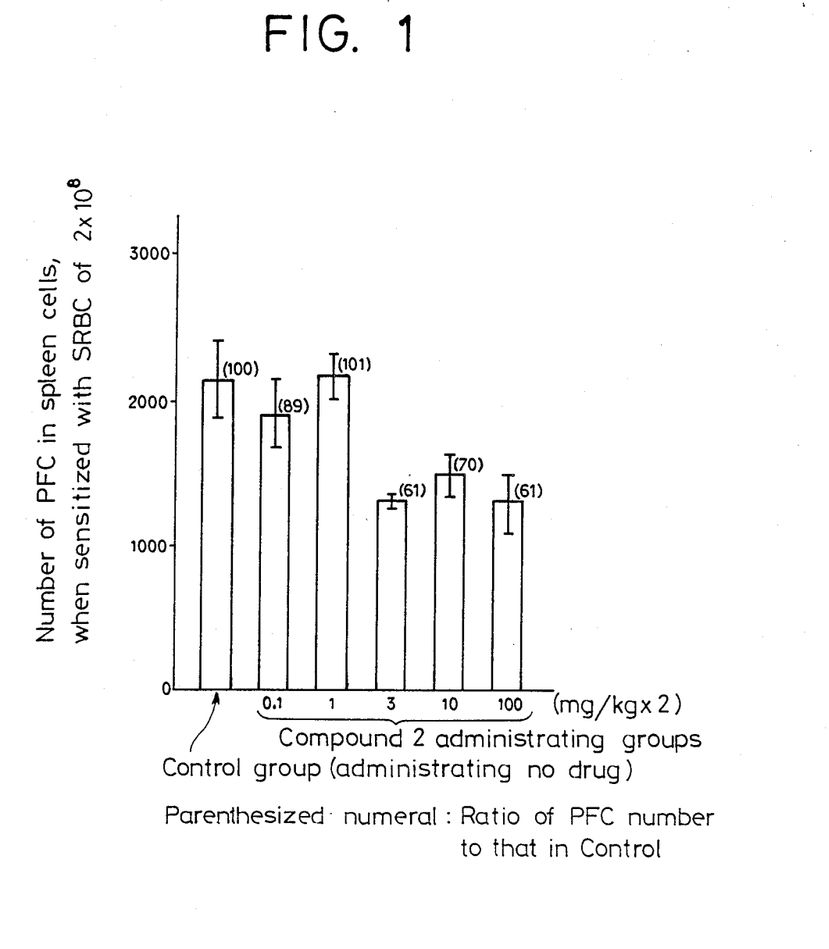
FIG. 1 is a graph showing results that a compound as effective ingredient for the composition according to the invention was administrated in various amounts to mice sensitized with antigen of $2 \times 10^8$ SRBC to check an antibody production ability, with an index of number of PFC in their spleen cells.
Figure 2:
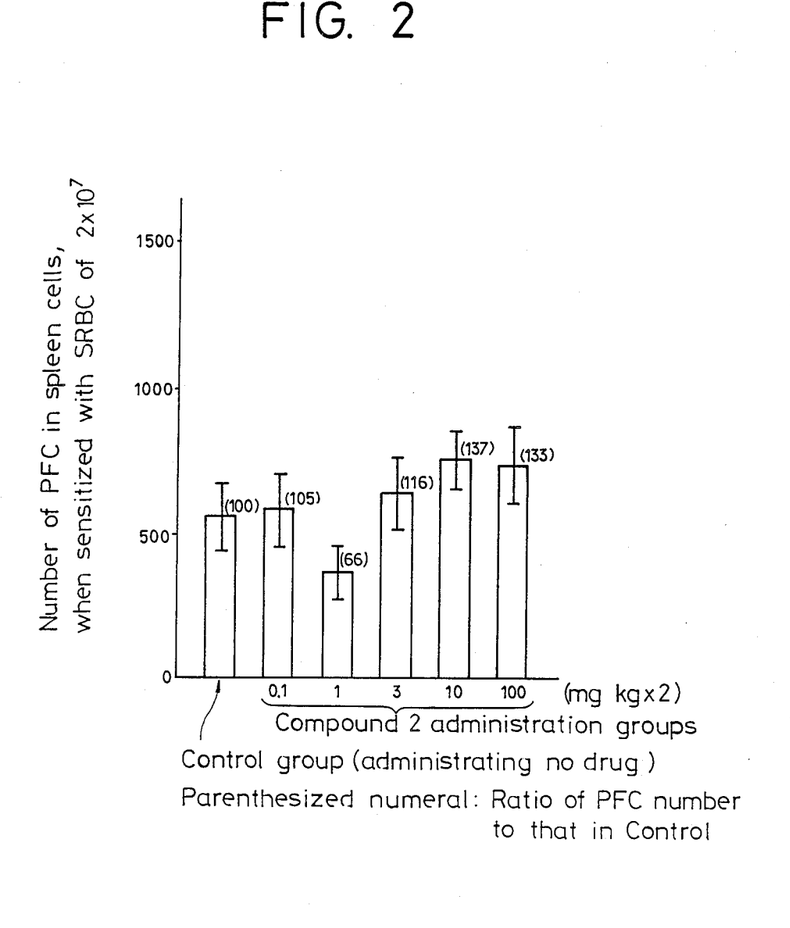
FIG. 2 is a graph showing results similar to FIG. 1, excepting that the mice were sensitized with the antigen of $2 \times 10^7$ SRBC.

Results in both systems sensitized with SRBC $2 \times 10^8$ pieces and $2 \times 10^7$ pieces are shown in FIGS. 1 and 2, respectively. As seen from the Figures, there are such tendencies that the PFC is decreased in the former system but in the latter system, the PFC is increased.

It is apparent from the results that the compound 2 develops the immunity controlling action.

PHARMACOLOGICAL TEST EXAMPLE 3

(Influence on juvenilization of lymphocyte)

(a) Object

An effect of the compound 2 to juvenilization of spleen cells in normal mice, which is to be caused by an action of mitogen is checked.

(b) Operation

To a culture medium (RPMZ 1640 medium containing 10% FCS) containing the compound 2 in 0.01 to 100 mg/ml, a suspension of spleen cells ($5 \times 10^5$/ml) on BALB/c female mouse was added, and then ConA, PHA or LPS as the mitogen was added. Thereafter, an amount of $^3$H-thymine taken into the spleen cells was determined to check the effect of the compound from the amount as an index therefor.

(c) Results and consideration

Figure 3A:
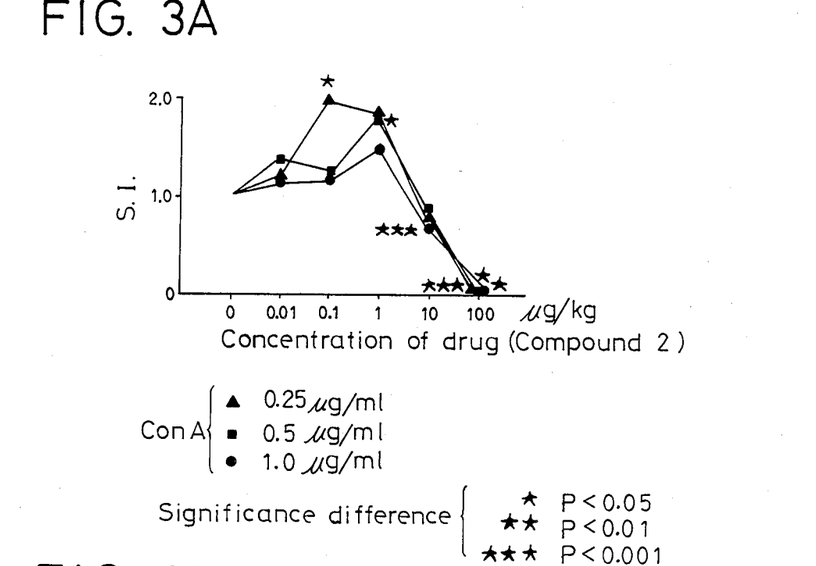
FIGS. 3A, 3B and 3C are graphs showing an influence of the compound upon a juvenilizing reaction in spleed cells caused by mitogen of ConA, PHA and LPS, which were indicated with stimulation index by amount of $^3$H-thymine.
Figure 3B:
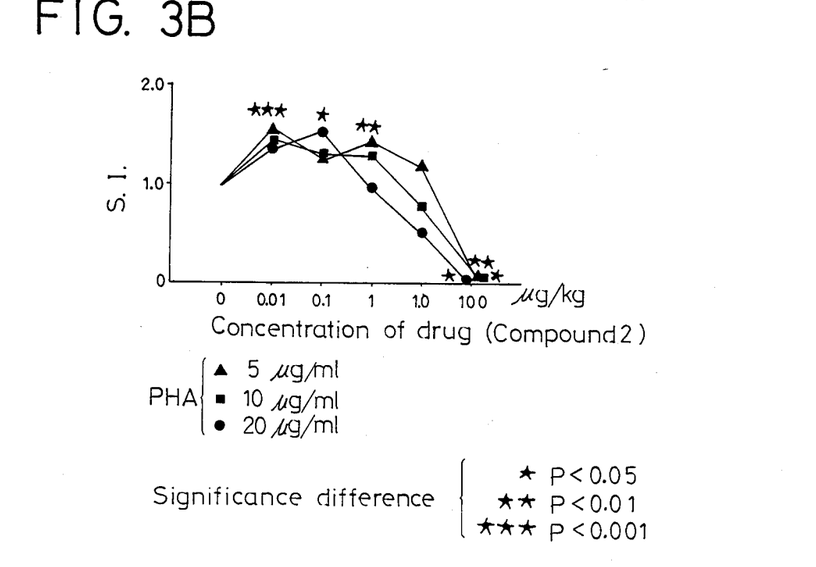
Figure 3C:
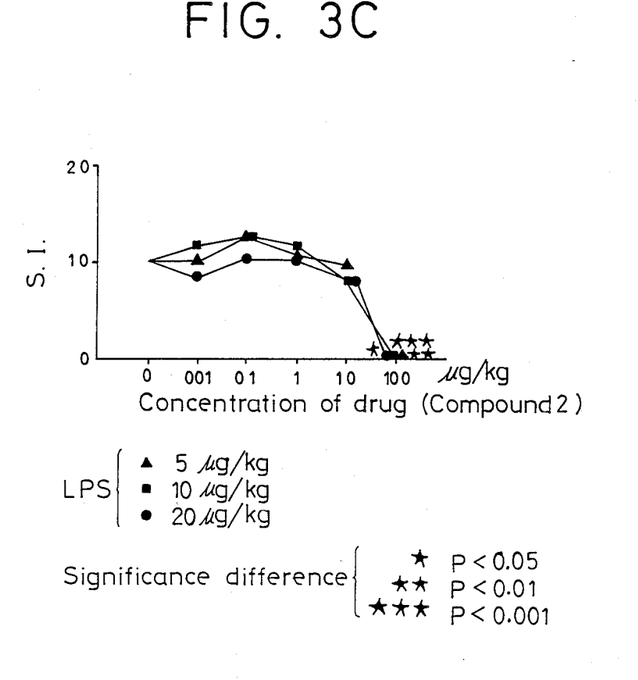

Results are shown in FIGS. 3A, 3B and 3C with a relation between a stimulation index and concentration of the compound. It can be seen from the Figures that the compound apparently accelerate the juvenilization of lymphocytes, due to ConA or PHA but remains only showing a tendency of acceleration, on that due to LPS.

This fact show that the influence of the compound 2 on immunity system develops through T-cells.

PHARMACOLOGICAL TEST EXAMPLE 4

(Action to adjuvant arthritis of rat)

(a) Object

An effect of the compound 2 on prevention of adjuvant arthritis is checked.

(b) Operation

An adjuvant (prepared by suspending 0.6 mg of killed mycobacterium-butiricum in 0.05 ml of fluid paraffin) was injected to SD female rats through calx skin of a hind leg to cause an arthritis. On each day after 1, 3, 5, 7, 14, 21 and 28 days from the adjuvant administration, a volume of the leg was measured to determine a ratio of edema (swelling). Moreover, an inflammation degree at the not treated hind leg, both front legs, ear and tail was measured on 14th, 21st and 28th day from the administration to evaluate by an index (score designation).

As to the group giving the tested drugs inclusive of the compound 2, the drug was orally administrated once a day by a predetermined amount over 28 days inclusive of that the adjuvant was injected.

(c) Results and consideration

Figure 4:
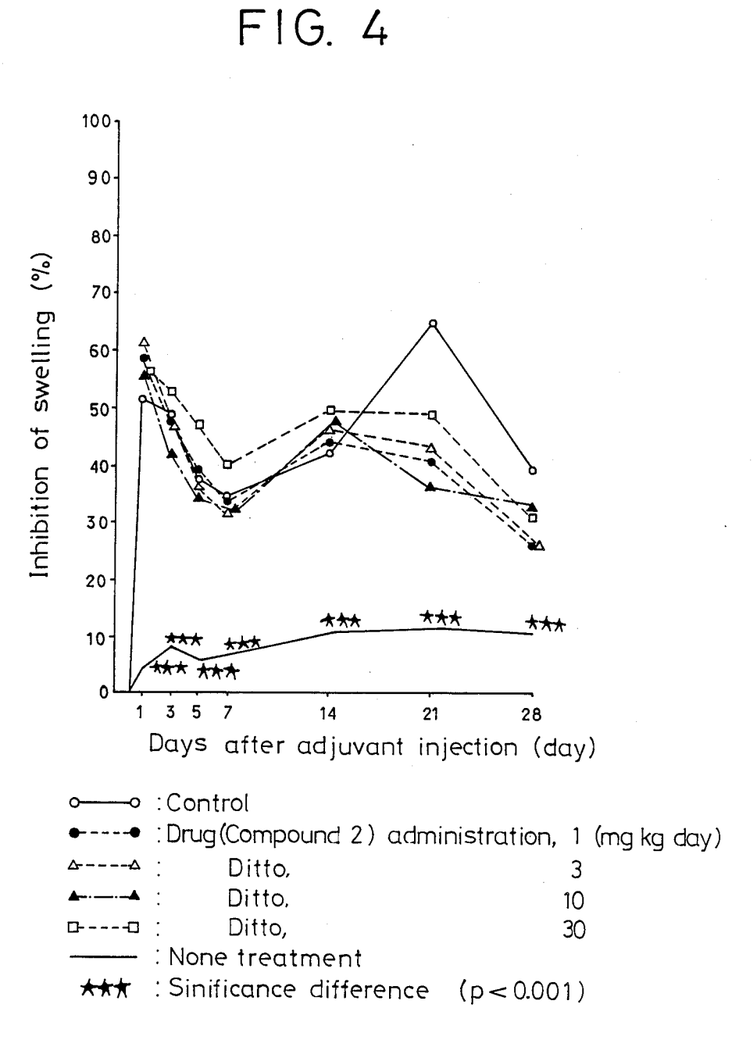
FIG. 4 is a graph showing results that an influence of the compound upon an adjuvant arthritis in rats was checked with an inhibition of swelling.

The results on inhibition of swelling and inflammation score are shown in FIG. 4 and following Table 3, respectively.

From FIG. 4, it can be seen that an effect of inhibition on the secondary inflammation develops on the groups, to which the compound 2 was given at 3 or 10 mg/kg. This inhibition effect is reflected to the results of the inflammation scores in Table 3 and an incidence of the swelling, which is shown in a parenthesis on the Table.

It is believed that a fact that the compound 2 inhibits not the primary but secondery swelling supports its immunity controlling action suggested from the results shown in Pharmacological Test Examples 2 and 3.

Figure 5:
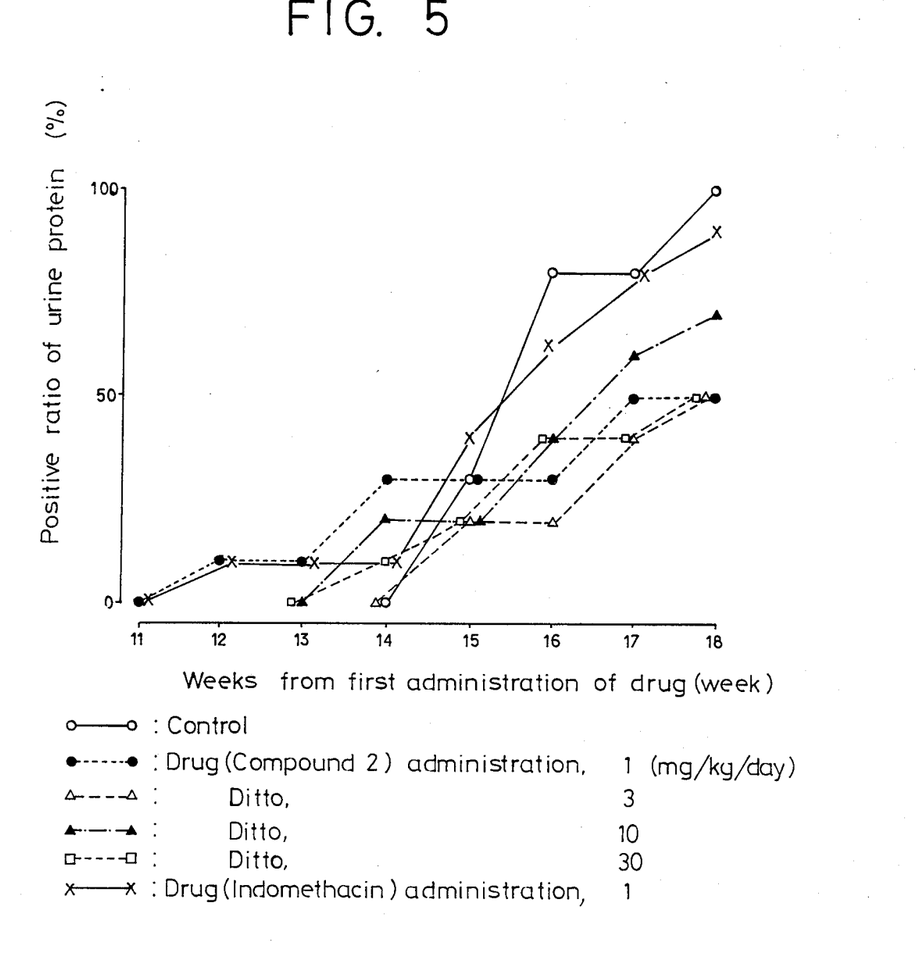
FIG. 5 is a graph showing results that the compound was administrated to self-immuno diseased mice to check an amount of urine protein with their positive ratio.
Figure 6:
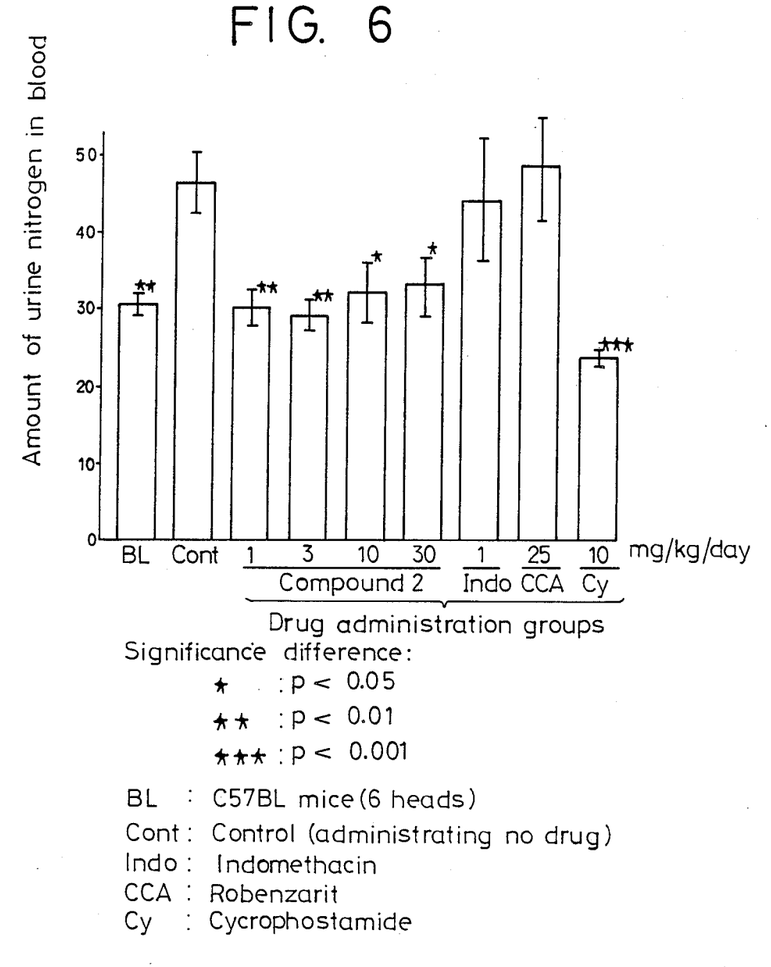
FIG. 6 is a graph showing results that the compound and other drugs was administrated to the self-immuno diseased mice to check an amount of urea nitrogen.
Figure 7:
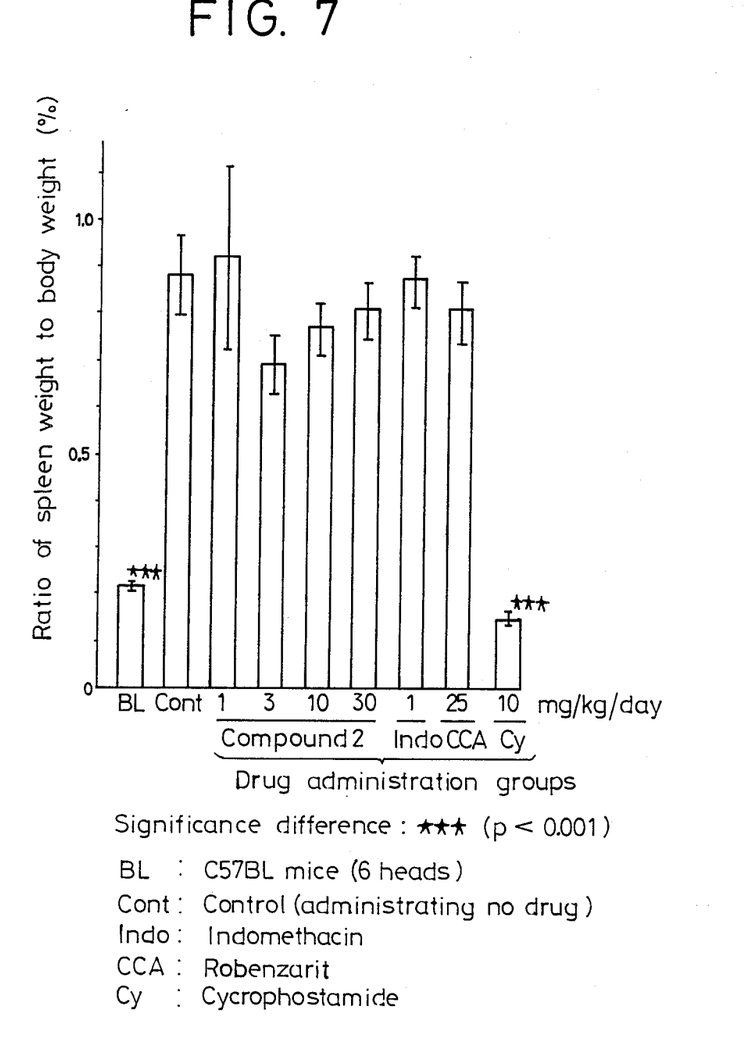
FIG. 7 is a graph showing results that the compound was administrated to the self-immuno diseased mice to check a ratio of spleen weight to the body weight.

In general non-steroid type anti-inflammation drugs, the actions as seen on the compound 2 can not be recognized and thus results as shown in FIGS. 5 to 7 support a fact that the compound 2 has the immunity controlling action suggested by the results of the Pharmacological Test Examples 2 and 3, together with the results of the Pharmacological Test Example 4.

What is claimed is:

TABLE 3

| Compound | Dose (mg/kg/day, p.o.) | Inflammation Score | | |
|---|---|---|---|---|
| | | 14th day | 21st day | 28th day |
| No (control) | — | 2.9 ± 0.8 (7/9) | 5.3 ± 1.1 (8/9) | 5.0 ± 1.0 (8/9) |
| Compound 2 | 1 | 5.0 ± 0.9 (9/10) | 5.6 ± 1.2 (8/10) | 4.8 ± 1.1 (8/10) |
| Compound 2 | 3 | 3.2 ± 1.0 (6/10) | 3.7 ± 1.2 (6/10) | 2.7 ± 1.0 (5/10) |
| Compound 2 | 10 | 3.7 ± 1.0 (7/10) | 5.5 ± 1.2 (9/10) | 7.0 ± 1.3 (8/10) |
| Compound 2 | 30 | 3.8 ± 1.1 (7/10) | 5.7 ± 1.4 (7/10) | 6.0 ± 1.6 (7/10) |
| Indomethacin | 1 | 2.0 ± 0.9 (4/10) | 2.4 ± 1.3 (3/10) | 2.2 ± 1.1 (4/10) |
| Diclofenac Na | 3 | 4.2 ± 1.1 (7/10) | 4.3 ± 1.2 (7/10) | 5.6 ± 1.3 (10/10) |
| Robenzarit | 25 | 3.6 ± 1.3 (5/10) | 4.7 ± 1.3 (7/10) | 5.4 ± 1.5 (7/10) |

PHARMACOLOGICAL TEST EXAMPLE 5

(Action to generation of self-immuno disease)

(a) Object

An action of the compound 2 for preventing from generation of self-immuno nephritis in MRL/1 mice is checked.

(b) Operation

To MRL/1 female mice (age of 6 weeks), the compound 2 was orally administered once a day in an amount of 1, 3, 10 or 30 mg/kg/day over 12 weeks. Within the testing period, a urine protein was measured once a week to check a positive ratio in each week, by determining as positive animal who shows the urine protein concentration of more than 100 mg/dl. Further, a urea nitrogen in blood was measured at the next day from the final administration to evaluate the action of the tested drugs inclusive of the compound 2 from serum biochemistrical view point and to check an influence on weight increase of the spleen.

(c) Results and consideration

Results on the positive ratio on urine protein and the urea nitrogen in blood are shown in FIGS. 5 and 6, respectively. From the Figures, it can be seen that the compound 2 inhibits the generation of nephritis and a preferable amount therefor is 3 mg/kg/day.

While, results on ratio of spleen weight to body weight are shown in FIG. 7. From the Figure, it can be considered that the compound 2 has a tendency for decreasing the ratio and a preferable amount therefor is 3 mg/kg/day.

Further, results of phatological analysis and an evaluation thereof are given in following Table 4.

1. A method for controlling immune response in an animal requiring such control which comprises administering to the animal an immune response-controlling amount of a compound of the formula wherein each of $R_1$ and $R_2$ is phenyl or p-halogenophenyl, and $R_3$ is hydrogen or methyl, or a pharmaceutically acceptable salt thereof.

2. A method as claimed in claim 1, wherein the compound is 3-(p-chlorophenyl)-1-phenylpyrazole-4-acetic acid or a pharmaceutically acceptable salt thereof.

3. A method as claimed in claim 2, wherein the pharmaceutically acceptable salt is the calcium salt.

4. A method for treating an immunity disease in an animal requiring such treatment which comprises administering to the animal an immune response-controlling amount of a compound of the formula

TABLE 4

| Item | Control | Compound A | | | | Indomethacin |
|---|---|---|---|---|---|---|
| | | 1 mg/kg | 3 mg/kg | 10 mg/kg | 30 mg/kg | 1 mg/kg |
| Number of animals | 10 | 10 | 10 | 10 | 10 | 10 |
| No. of observed glomerulus | 100 | 100 | 100 | 100 | 100 | 100 |
| Glomerulosclerosis | 1 | 0 | 0 | 0 | 0 | 1 |
| Glomerulocapsular nephritis | | | | | | |
| Heavy | 13 | 7 | 1 | 2 | 4 | 4 |
| Medium | 43 | 25 | 22 | 27 | 30 | 52 |
| Light | 42 | 56 | 66 | 68 | 54 | 42 |
| Normal | 1 | 12 | 11 | 3 | 12 | 1 |
| Analysis of variance | | ** | *** | ** | ** | |

Significance Difference:
*$p < 0.05$, $p < 0.01$, *$p < 0.001$ wherein each of $R_1$ and $R_2$ is phenyl or p-halogenophenyl, and $R_3$ is hydrogen or methyl, or a pharmaceutically acceptable salt thereof.

5. A method as claimed in claim 4, wherein the compound is 3-(p-chlorophenyl)-1-phenylpyrazole-4-acetic acid or a pharmaceutically acceptable salt thereof.

6. A method as claimed in claim 5, wherein the pharmaceutically acceptable salt is the calcium salt.

* * * * *